United States Patent
Candidus

(10) Patent No.: US 8,604,784 B2
(45) Date of Patent: Dec. 10, 2013

(54) CUSHION FOR A PATIENT BED IN A MEDICAL IMAGING APPARATUS

(75) Inventor: Yvonne Candidus, Tuchenbach (DE)

(73) Assignee: Siemens Aktiengesellschaft, Munich (DE)

( * ) Notice: Subject to any disclaimer, the term of this patent is extended or adjusted under 35 U.S.C. 154(b) by 506 days.

(21) Appl. No.: 12/881,544

(22) Filed: Sep. 14, 2010

(65) Prior Publication Data

US 2011/0074424 A1  Mar. 31, 2011

(30) Foreign Application Priority Data

Sep. 30, 2009 (DE) .......... 10 2009 047 796

(51) Int. Cl.
*G01V 3/00* (2006.01)

(52) U.S. Cl.
USPC .......................................... 324/307

(58) Field of Classification Search
USPC ................................. 324/300–322
See application file for complete search history.

(56) References Cited

U.S. PATENT DOCUMENTS

| | | |
|---|---|---|
| 5,809,597 A | 9/1998 | Shaw |
| 7,180,294 B2 * | 2/2007 | Kohlmuller .................. 324/318 |
| 2007/0038070 A1 | 2/2007 | Tank |
| 2007/0225588 A1 * | 9/2007 | Steckner ...................... 600/407 |
| 2009/0264735 A1 * | 10/2009 | Steckner ...................... 600/422 |
| 2009/0286478 A1 | 11/2009 | Biber et al. |

FOREIGN PATENT DOCUMENTS

| | | |
|---|---|---|
| DE | 198 54 928 A1 | 6/2000 |
| DE | 103 08 874 A1 | 7/2004 |
| JP | 2009165733 A * | 7/2009 |

* cited by examiner

Primary Examiner — Dixomara Vargas
(74) Attorney, Agent, or Firm — Schiff Hardin LLP

(57) ABSTRACT

An MRT acquisition can be simplified by a method, an MRT apparatus and a support, for example a cushion, for a magnetic resonance tomography examination, that has at least one positioning aid for a heel of the patient and that has at least one positioning aid for the head.

15 Claims, 2 Drawing Sheets

CUSHION FOR A PATIENT BED IN A MEDICAL IMAGING APPARATUS

BACKGROUND OF THE INVENTION

1. Field of the Invention

The invention concerns an insert in the form of a support or a cushion for a magnetic tomography (MRT) patient bed, an MRT apparatus embodying such a cushion, and a method for operating such an MRT apparatus.

2. Description of the Prior Art

A magnetic resonance tomography arrangement is known from the Patent Application DE 10 2008 023 467, for example.

SUMMARY OF THE INVENTION

An object of the present invention to simplify magnetic resonance tomography acquisitions.

The above object is achieved in accordance with the present invention by a method for conducting a magnetic resonance tomography examination wherein a patient is positioned with the patient's head, or at least one heel, in a positioning aid of a support on a patient bed. The positioning aid is located on the patient bed so that when the patient is moved on the patient bed into the acquisition region of a magnetic resonance tomography apparatus by movement of the patient bed, a desired image region of the patient, of which a magnetic resonance exposure is to be obtained, is appropriately located in the magnetic resonance tomography apparatus.

The invention also encompasses a magnetic resonance tomography apparatus for implementing the method described above.

DESCRIPTION OF THE PREFERRED EMBODIMENTS

Figure 1:
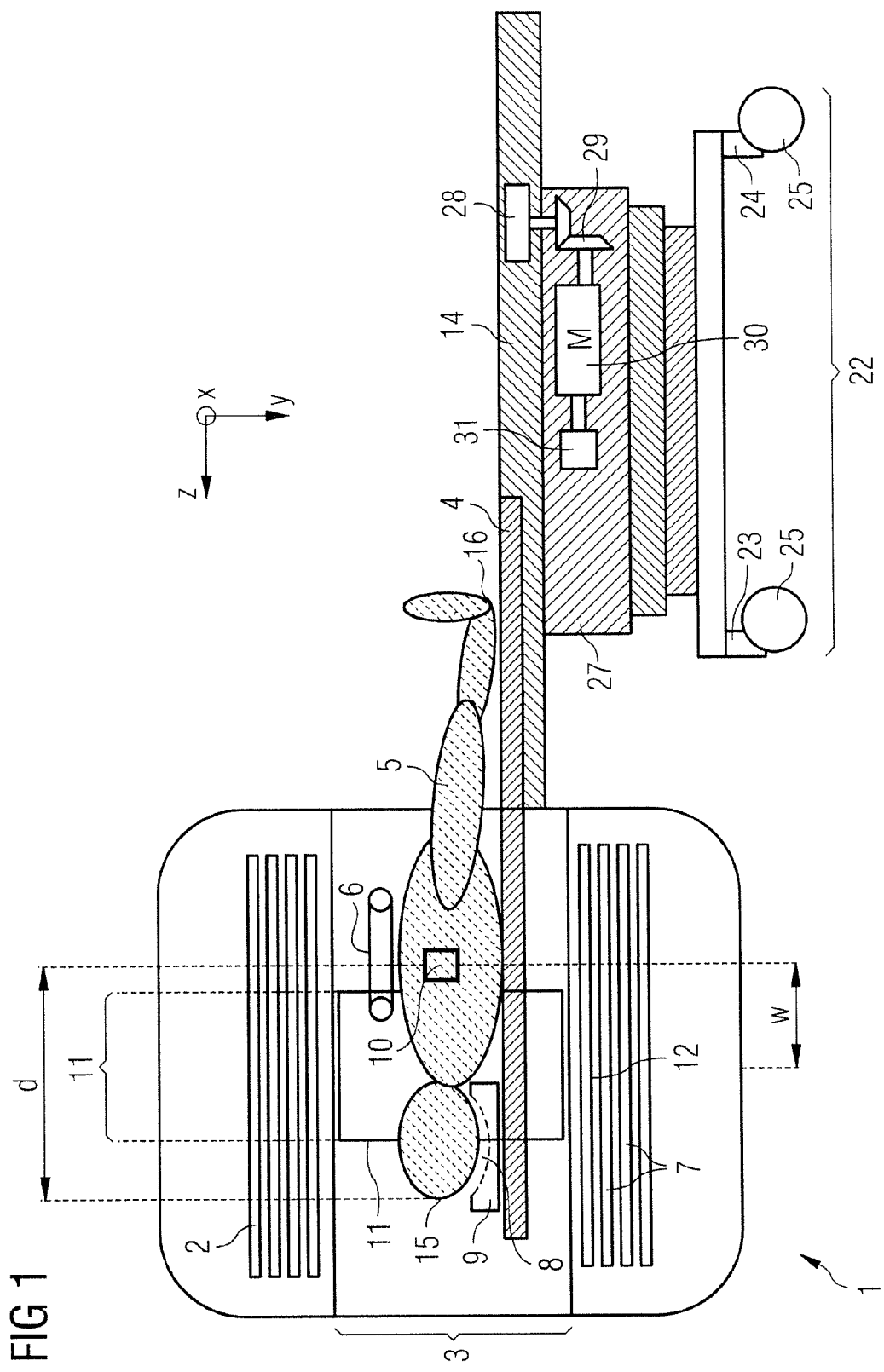
FIG. 1 schematically illustrates a magnetic resonance tomography (MRT) whole-body coil.

As an overview depiction, FIG. 1 shows, in a highly simplified manner and not to scale, a magnetic resonance apparatus MRT 1 with a whole-body coil 2 with a tube-shaped space 3 into which a patient bed 4 (a patient table), for example with a patient 5 and a local coil arrangement 6, can be driven in the direction of the arrow z in order to generate MRT exposures of the patient 5. Here a local coil array 6 (with multiple local coils and channels for signals from the local coils) with which exposures can be generated in a local region is placed on the patient 5. The signals of these exposures can be evaluated (reconstructed into images, etc.) by a known evaluation device that can be connected via coaxial cables etc. The activation of a slice plane through the patient that is to be exposed ensues by the operation of gradient coil systems 7 (shown in part) for the x-/y-/z-axis. An RF antenna 12 is indicated for the generation of RE sequences.

The head (or the feet) of the patient here lies in a recess 8a (or the feet in recesses 8b, 8c) of a support 9 fashioned as a cushion that is arranged so that it cannot slip to any significant degree. It is secured in terms of position so that, based on a model of the patient (that, for example, can include the patient's measured body size and/or body shape, etc.), the position of an image region 10 (such as the liver or the heart) of the patient of which an image should be acquired can be driven or moved by an actuator (drive) 28, 29, 30 (controlled by a controller 31) of the patient bed 4 over a distance w in the acquisition region 11 of the MRT 1. The patient bed 4 can be displaced on a patient table 14 which is supported on a frame 27, 23, 24 with wheels 25, 26. The controller 31 of the actuator 28, 29, 30 of the patient bed 4 can be controlled by a central controller of the MRT 1, and the position of the patient bed 4 can be read out from there.

Figure 2C:
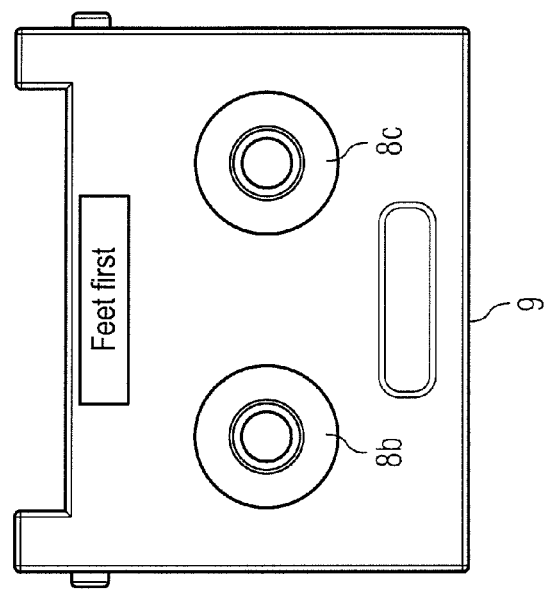
FIG. 2C shows the support of FIGS. 2A and 2B in a view from below.
Figure 2B:
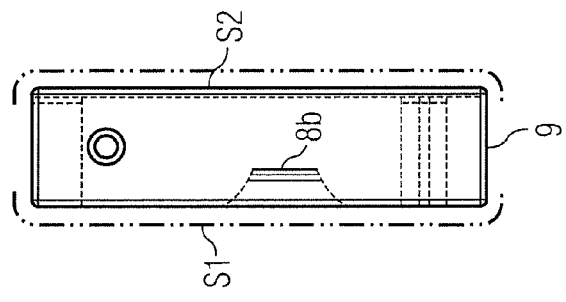
FIG. 2B shows the support of FIG. 2A in cross-section.
Figure 2A:
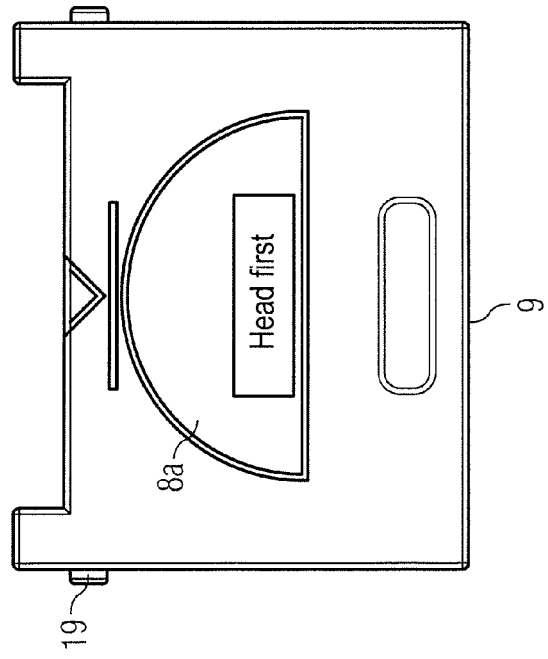
FIG. 2A schematically illustrates a support fashioned as a cushion in accordance with the present invention, in plan view.
Figure 2D:
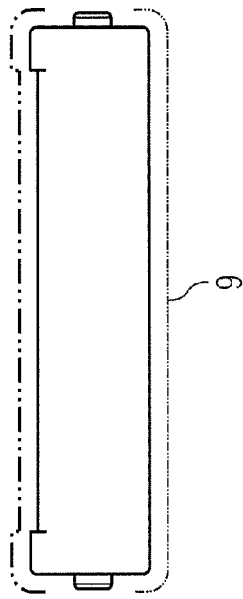
FIG. 2D shows the support of FIGS. 2A, 2B and 2C from a side thereof.

FIGS. 2A-2D schematically show (with only examples of measurement specifications in mm) a support 9 (fashioned as a cushion) with recesses 8a, 8b, 8c as positioning aids. This is shown in plan view (FIG. 2A), in cross section (FIG. 2B), as a view from below (FIG. 2C) and in a side view (FIG. 2D).

FIG. 2A shows in plan view a recess 8a in a cushion 9 in which the head 15 of the patient can be positioned, and also a label "Head first" as an aid to users.

FIG. 2C shows two recesses 8b, 8c in a cushion 9 in which a foot (for example a heel 16) is respectively to be positioned via insertion into the recesses, and a label "Feet first" as an aid to users. FIG. 2B shows the cushion of FIGS. 2A and 2C in cross section. FIG. 2D shows the cushion of FIGS. 2A and 2C in longitudinal section.

The cushion here has on a top side S2 (FIG. 2A) a positioning aid 8a suitable for the head in the form of a recess and, on an underside S1 (FIG. 2C) opposite the top side, suitable positioning aids 8b, 8c in the form of two recesses for the feet (in particular heels 16).

Fixing devices allow the cushions to be fixed against unintentional displacement in the patient bed 4, for example pins 19 of the cushion that can be inserted into recesses on the side of the patient bed 4, etc.

The support can be a cushion or another retention device of arbitrary design, thus be hard or soft, elastic or rigid etc.

The recesses 8a, 8b, 8c can have very different shapes.

Instead of or in addition to recesses, other or additional positioning aids can be provided for head and feet; loops are conceivable, for example.

Before a magnetic resonance tomography examination, if a patient is positioned with his or her head or at least one heel 16 on a positioning aid (recess 8a, 8b, 8c) of the support 9 on a patient bed 4, via the retention device in the form of a cushion 9 (for example) allows a desired image region 10 (for example an organ 10 such as the heart or the liver) of the patient of which (10) an exposure should be made to be driven into an acquisition region 11 of a magnetic resonance tomography apparatus 1 by movement (z) of the patient bed 4 on the (stationary) patient table 14 with an actuator 28, 29, 39, M (formed by a motor and a gearing, for example) controlled by a controller 31 (symbolically illustrated).

An automatic start of the measurement (for example for liver examinations) is possible even given the use of non-stationary local coils 6 (for example a body matrix) on the patient bed 4.

The MRT system can automatically detect the position of the patient on the patient bed 4.

According to the invention, the MRT measurement (for example of the heart or the liver) can be started automatically with the assistance of an anatomical model. For this purpose, the precise position of the crown or head (given "head first, insertion of the patient into the MRT with the head first) or the position of the heel 16 (given "feet first", insertion of the patient into the MRT with the feet first) can be detected. Here the invention allows the head or the heel 16 to be supported in a stationary manner on the patient bed 4.

The cushion 9 here is a combined head/heels cushion that is simple to operate.

This cushion here is located stationary between the plug panels of the MRT patient bed 4.

A recess for a fixed positioning of the head is located on the one side of the cushion; therefore the head is located stationary on the patient bed 4. The cushion can be rotated (flipped). Due to the rotation capability of the cushion, the feet do not come to lie on the same side as the head, which has hygienic advantages. Two recesses 8b, 8c for the stationary positioning of the heels 16 are located on the side opposite the head positioning. With the use of the cushion the patient can thus be positioned in an approximately stationary manner on the patient bed 4 and, for example, the position of the liver of the patient can be determined by means of the anatomical model. For example, the liver of the patient can be driven automatically into the center 11 of the MRT 1 and the measurement can start automatically.

It is possible to attach sensors to the cushion and/or to the patient bed 4, which sensors establish how the cushion lies on the patient bed 4, and therefore whether the recesses for the head or the feet are situated on top, and to transmit this information to a controller 31 for an actuator of the patient bed 4 so that this controller 11 can use this information (at least as a first attempt) for the positioning of the image region 10 (liver etc.) of the patient in the acquisition region 11 of the magnetic resonance tomography apparatus (of which desired image region 10 an exposure should be made). Here it is also conceivable to query via a keyboard how the cushion is situated.

The anatomical model of the patient can, in the simplest case represent information, for example the size of the patient to be measured with a measuring tape etc., and a rough measure of the distance from the acquisition region 11 (in the liver, the region at the right costal arch at which the liver is located) to the support point of the back of the head in the recess 8a or crown (or heel support point or sole of the foot). These values are entered into the controller 31 of the patient bed actuator so that the controller 31 calculates the displacement path w of the patient bed 4. Anatomical models and patient dimension measurement methods are, however, typically significantly more detailed and precise.

Although modifications and changes may be suggested by those skilled in the art, it is the intention of the inventor to embody within the patent warranted hereon all changes and modifications as reasonably and properly come within the scope of her contribution to the art.

I claim as my invention:

1. A method for conducting a magnetic resonance tomography examination of a patient, comprising the steps of:
   positioning a head or at least one heel of a patient in a positioning aid of a support on a patient bed;
   locating said support on said patient bed to cause a predetermined image region of the patient, from which magnetic resonance data are to be obtained, to be located in an acquisition region of a magnetic resonance tomography apparatus when the patient bed is moved into the magnetic resonance tomography apparatus;
   rotating said support by 180° to selectively position a configuration in said positioning aid conforming to the head or at least one heel of the patient; and
   moving the patient, positioned with the support on the patient bed into said acquisition region of said magnetic resonance tomography apparatus, and acquiring magnetic resonance data from said image region.

2. A method as claimed in claim 1 comprising, in a processor, determining a path through which the patient is moved to move the image region into the acquisition region, using a patient model comprising dimensions of the patient.

3. A method as claimed in claim 1 comprising determining a path by which the patient is moved to move the image region into the acquisition region dependent on whether the head or at least one heel of the patient is positioned in the positioning aid of the support.

4. A method as claimed in claim 1 comprising determining a path by which the patient is moved to move the image region into the acquisition region dependent on a distance of the image region from either the head in the positioning aid or said at least one heel in the positioning aid.

5. A method as claimed in claim 1 comprising positioning the support at a stationary location on the patient bed on which the patient is also positioned.

6. A method as claimed in claim 1 comprising selecting said image region that contains an organ of interest of the patient.

7. A support for a patient undergoing a magnetic resonance tomography examination, said support comprising:
   a support body;
   at least one positioning aid formed as a depression in said support body configured to receive a heel of a patient; and
   at least one positioning aid formed in said support body configured to receive the head of a patient.

8. A support as claimed in claim 7 wherein said support body is formed as a cushion.

9. A support for a patient undergoing a magnetic resonance tomography examination, said support comprising:
   a support body comprising a fixing device configured to affix the support body to a patient bed that precludes horizontal displacement of said support body relative to said patient bed;
   at least positioning aid formed in said support body configured to receive a heel of a patient; and
   at least one positioning aid formed in said support body configured to receive the head of a patient.

10. A magnetic resonance tomography apparatus comprising:
    a data acquisition device configured to receive a subject therein, said data acquisition device comprising an acquisition region from which magnetic resonance tomography data are best obtained;
    a patient bed configured to receive a patient thereon, said patient bed being movable into the data acquisition unit relative to the acquisition region;
    a support comprising a support body located on the patient bed, said support body comprising at least one position aid formed as a depression in said support body configured to receive a heel of the patient, and at least one positioning aid formed in said support body configured to receive the head of the patient; and
    a patient bed displacement controller configured to move the patient bed relative to the acquisition region to cause an image region of the patient to be positioned in the acquisition region, dependent on a position of the support on the patient bed.

11. A support for a patient undergoing a magnetic resonance tomography examination, said support comprising:
    a support body;

at least one positioning aid formed in said support body configured to receive a heel of a patient; and at least one positioning aid formed as a depression in said support body configured to receive the head of a patient.

12. A support for a patient undergoing a magnetic resonance tomography examination, said support comprising:

a support body;

two positioning aids formed in said support body configured to receive the respective heels of a patient, said two positioning aids being located at a first side of said support body; and at least one positioning aid formed in said support body configured to receive the head of a patient, said at least one positioning aid configured to receive the head of a patient being located at a second side of said support body, opposite said first side.

13. A magnetic resonance tomography apparatus comprising:

a data acquisition device configured to receive a subject therein, said data acquisition device comprising an acquisition region from which magnetic resonance tomography data are best obtained;

a patient bed configured to receive a patient thereon, said patient bed being movable into the data acquisition unit relative to the acquisition region;

a support comprising a support body located on the patient bed, said support body comprising at least one position aid formed in said support body and configured to receive a heel of the patient, and a positioning aid formed as a depression in said support body configured to receive the head of the patient; and a patient bed displacement controller configured to move the patient bed relative to the acquisition region to cause an image region of the patient to be positioned in the acquisition region, dependent on a position of the support on the patient bed.

14. A magnetic resonance tomography apparatus comprising:

a data acquisition device configured to receive a subject therein, said data acquisition device comprising an acquisition region from which magnetic resonance tomography data are best obtained;

a patient bed configured to receive a patient thereon, said patient bed being movable into the data acquisition unit relative to the acquisition region;

a support comprising a support body located on the patient bed, said support body comprising two positioning aids formed in said support body respectively for respective heels of the patient, located at a first side of said support body, and a positioning aid formed in said support body configured to receive the head of a patient, located at a second side of said support body opposite said first side; and a patient bed displacement controller configured to move the patient bed relative to the acquisition region to cause an image region of the patient to be positioned in the acquisition region, dependent on a position of the support on the patient bed.

15. A magnetic resonance tomography apparatus comprising:

a data acquisition device configured to receive a subject therein, said data acquisition device comprising an acquisition region from which magnetic resonance tomography data are best obtained;

a patient bed configured to receive a patient thereon, said patient bed being movable into the data acquisition unit relative to the acquisition region;

a support body comprising a fixing device configured to affix said support body to the patient bed that precludes horizontal displacement of said support body relative to said patient bed; and a patient bed displacement controller configured to move the patient bed relative to the acquisition region to cause an image region of the patient to be positioned in the acquisition region, dependent on a position of the support on the patient bed.

* * * * *